United States Patent [19]

Vidal

[11] Patent Number: 4,954,665
[45] Date of Patent: Sep. 4, 1990

[54] METHANOL HOMOLOGATION

[75] Inventor: Jose' L. Vidal, Kanawha, W. Va.

[73] Assignee: Union Carbide Chemicals and Plastics Company Inc., Danbury, Conn.

[21] Appl. No.: 900,275

[22] Filed: Aug. 27, 1986

Related U.S. Application Data

[63] Continuation of Ser. No. 795,725, Nov. 7, 1985, abandoned, which is a continuation of Ser. No. 653,050, Sep. 21, 1984, abandoned.

[51] Int. Cl.$^5$ .............................................. C07C 29/34
[52] U.S. Cl. ................................................... 568/902.2
[58] Field of Search ...................................... 568/902 H

[56] References Cited

U.S. PATENT DOCUMENTS

| | | | |
|---|---|---|---|
| 3,248,432 | 4/1966 | Riley et al. | 568/902 |
| 3,285,948 | 11/1966 | Butter | 568/902 |
| 4,111,837 | 9/1978 | Taylor . | |
| 4,133,966 | 1/1979 | Pretzer et al. | 568/902 |
| 4,233,466 | 11/1980 | Fiato . | |
| 4,239,924 | 12/1980 | Pretzer et al. | 568/902 |
| 4,239,925 | 12/1980 | Pretzer et al. | 568/902 |
| 4,253,987 | 3/1981 | Fiato . | |
| 4,277,634 | 7/1981 | Walker | 568/902 |
| 4,304,946 | 12/1981 | Isogai et al. . | |
| 4,306,091 | 12/1981 | Gauthier-Lafaye et al. . | |
| 4,324,927 | 4/1982 | Garthier-Lafaye et al. | 568/902 |
| 4,328,379 | 5/1982 | Devon . | |
| 4,348,541 | 9/1982 | Doyle | 568/902 |
| 4,352,946 | 10/1982 | Pretzer et al. | 568/902 |
| 4,352,947 | 10/1982 | Habib et al. | 568/902 |
| 4,357,480 | 11/1982 | Barlow et al. | 568/902 |
| 4,380,681 | 4/1983 | Barclay et al. | 568/902 |
| 4,389,532 | 6/1983 | Larkins, Jr. et al. | 568/902 |
| 4,407,404 | 10/1983 | Pretzer et al. | 568/902 |
| 4,424,383 | 1/1984 | Cornils et al. | 568/902 |
| 4,472,526 | 9/1984 | Cornils et al. | 568/902 |
| 4,552,986 | 11/1985 | Irogsi et al. | 568/902 |

FOREIGN PATENT DOCUMENTS 2083465  3/1982  United Kingdom .

*Primary Examiner*—J. E. Evans
*Attorney, Agent, or Firm*—Reynold J. Finnegan

[57] ABSTRACT

Process for production of ethanol at high efficiency, selectivity and conversion rate by the homologation reaction of methanol and carbon monoxide and hydrogen using a catalyst system containing alkali metal atom, cobalt atom, iodine atom and, optionally, ruthenium atom and an organic tertiary amino compound.

2 Claims, No Drawings

METHANOL HOMOLOGATION

This application is a continuation of prior U.S. application Ser. No. 795,725, filed Nov. 7, 1985, now abandoned, which is a continuation of application Ser. No. 653,050, filed Sept. 21, 1984, now abandoned.

BACKGROUND OF THE INVENTION

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of acetic acid, to our knowledge it does not disclose or suggest our invention. Several of the pertinent patents in this area are discussed below.

U.S. Pat. No. 4,133,966, filed by Wayne R. Pretzer et al and issued Jan. 9, 1979, discloses the process for the homologation of methanol to ethanol using a catalyst system containing cobalt acetylacetonate, a trivalent phosphorus or trivalent arsenic or trivalent antimony organic ligand, an iodine compound and a ruthenium compound. This is not the system employed in the instant invention.

U.S. Pat. No. 4,111,837, filed by Paul D. Taylor and issued on Sept. 5, 1978, relates to the use of a heterogeneous co-catalyst system for the homologation of alkanols. The co-catalyst system contains cobalt and rhenium metal. The catalyst disclosed is not the catalyst of the instant invention and, further, there is no mention of the use of an alkali metal atom.

In U.S. Pat. No. 4,233,466 and U.S. Pat. No. 4,253,987, filed by Rocco A. Fiato and issued on Nov. 11, 1980 and Mar. 3, 1981, respectively, there are disclosed processes and catalysts for the production of ethanol by the homologation reaction of methanol and synthesis gas using a system containing cobalt atom, ruthenium atom, iodine atom and a phosphine ligand. There is no disclosure or suggestion in these references of the advantages to be realized by the addition of an alkali metal atom.

U.S. Pat. No. 4,239,924 and U.S. Pat. No. 4,239,925, filed by Wayne R. Pretzer et al and issued on Dec. 16, 1980, disclose a process for selectively producing ethanol using a system containing a specifically defined cobalt tricarbonyl complex, an iodine compound, and a ruthenium compound in the methanol homologation reaction. The basic distinction between the two patents is the use of aliphatic substituted complexes in U.S. Pat. No. 4,239,924 and aromatic substituted complexes in U.S. Pat. No. 4,239,925. Neither patent makes any mention or suggestion on the use of an alkali metal atom in the process.

U.S. Pat. No. 4,324,927, filed by Jean Gauthier-Lafaye et al and issued on Apr. 13, 1982, describes a process for the homologation of methanol to produce ethanol using a system containing cobalt atom, ruthenium atom and both an alkyl halide and an ionic halide.

U.S. Pat. No. 4,304,946, filed by Nobuo Isogai and issued on Dec. 8, 1981, describes the homologation of methanol to produce ethanol using a cobalt sulfide compound or a mixture of a cobalt sulfide compound and a nitrogen-containing and/or a phosphorus containing compound. The system is free of iodine atom.

U.S. Pat. No. 306,091, filed by Jean Gauthier-Lafaye and issued on Dec. 15, 1981, describes the carbonylation of methanol to produce acetaldehyde using a system containing cobalt atom, ruthenium atom, ionic halide and an alkyl halide wherein the cobalt concentration is at most 50 mgm atoms per liter of reaction. The emphasis in this patent is the production of acetaldehyde and only trace amounts of by-product ethanol are shown to be produced. On the other hand, in this instant application ethanol is the desired product.

U.S. Pat. No. 4,328,379, filed by F. J. Devon and issued on May 4, 1982, describes the homologation of methanol to produce ethanol using a cobalt-iodine catalyst system in the presence of a perfluorocarboxylate anion. There is no disclosure of the presence of ruthenium and alkali metal atom in the catalyst system.

U.K. Patent Application GB 2,083,465A, filed by N. Isogai et al and published on Mar. 24, 1982, for the homologation of methanol to produce ethanol using a heterogeneous catalyst system comprising cobalt phosphate as the main catalyst. The applicants also disclose the use of a Group VIII metal as co-catalyst. They do not mention any use of an alkali metal atom in the catalyst system.

SUMMARY OF THE INVENTION

A process for the production of ethanol at high efficiency, selectivity and conversion rate by the homologation reaction of methanol and carbon monoxide and hydrogen has been found. The catalyst system charged to the reactor in our process contains alkali metal atom, cobalt atom, iodide atom and optionally ruthenium atom and an organic tertiary amino compound as co-promoter. The use of alkali metal atom in this system within the ranges defined results in unexpectedly high efficiency, high conversion rate or activity, and high selectivity not heretofore achieved.

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect, or precipitating out of solution.

Activity or conversion rate relates to the amounts of reactants the catalyst converts to product per unit of time, generally expressed in g. mole per liter per hour (g mole/1/hr).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective, improvement is always desirable.

The present invention is based on the unexpected and unpredictable discovery that the catalyst system of this invention, which requires the presence of an alkali metal atom in conjunction with cobalt atom and iodide atom or in conjunction with cobalt atom and ruthenium atom and iodide atom is an unexpectedly superior catalytic system for the production of ethanol from methanol and synthesis gas at unexpected high efficiency, selectivity and conversion rate. It was also found that a co-promoter, $R_3N_1$, can also be present as an optional component of the system. This unexpected improvement in efficiency, selectivity and conversion rate is achieved when the system's components are maintained within a defined range and when the alkali metal atom is present in the system. Optionally a solvent and/or diluent can also be present. The iodine atom is present in the form of acidic iodide atom.

In the process of our invention methanol is reacted with synthesis gas in the presence of the inventive catalyst system. This catalyst system produces commercially desirable ethanol at unexpectedly high efficiency, conversion rate and selectivity, with a minimum of by-products. The overall reaction that occurs is theoretically:

$$CH_3OH + CO + 2H_2 \rightarrow CH_3CH_2OH + H_2O$$

The Co - I - Alkali Metal ($R_3N$ Optional) System A

One of the systems found useful in the reaction of methanol with mixtures of carbon monoxide and hydrogen is the system containing cobalt atom, acidic iodine atom, alkali metal atom and optionally, tertiary amine (hereinafter "System A").

At temperatures of from about 165° C. to about 180° C. this System A selectively produced acetaldehyde and dimethylacetal, an hydroformylation reaction, while at about 190° C. to about 220° C. System A selectively produced ethanol, an homologation reaction.

The addition of alkal metal atom (in the form, e.g., of sodium bicarbonate, sodium iodide, sodium tetraborate) and tributylamine to the cobalt atom-iodine atom mixture improved the stability of cobalt and the selectivity and rate of formation of ethanol at temperatures of from 190° C. to 220° C. The precipitation of cobalt at 190° C. to 220° C. observed with cobalt atom-iodine atom systems was inhibited by the addition of the alkali metal and amine compounds. Though cobalt precipitation was inhibited up to 220° C., cobalt precipitation was not precluded at higher temperatures with system A.

At temperatures below 190° C., specifically at about 165° C. to 180° C., the reaction was not an homologation reaction, rather an hydroformylation reaction predominated with acetaldehyde and dimethylacetal formed as the major selectively produced products together with significant amounts of methyl acetate.

From the data obtained it was concluded temperature has a material effect on both the reaction that will occur and the products that are obtained as well as on the stability of the cobalt compound by the use of homogeneous catalyst mixture System A.

The stability of System A was completely unexpected and unpredictable. It was observed homogeneous solutions of System A maintained their homogeneity for periods of two to three days after they had been used in a catalytic run. In addition, it was found that solutions of the cobalt, iodine and alkali metal components in methanol heated at 90° C. to 100° C. under 5,000 psig CO:H (1:1) for 10 minutes provided homogeneous solutions which did not precipitate solids of ambient room conditions for periods up to about 90 hours. These solutions, after addition of the amine compound, were still catalytically active and homogeneous.

A further advantage of System A is that it does not require the use of a triorgano phosphine, and, thus, it avoids the problems associated with the decomposition of such phosphine compounds, e.g., changes in catalytic activity or selectivity with time. Another advantage of System A is the long term catalyst stability and the diminution of cobalt precipitation problems in continuous reactor operations. Cobalt precipitation is of significant concern with phosphine-containing systems in continuous operations but is of lesser concern with System A when it is used at our defined conditions.

The Co-Ru-I-Alkali Metal ($R_3N$ Optional) System B

Another system found useful for the reaction of methanol with mixtures of carbon monoxide and hydrogen is the system containing cobalt atom, ruthenium atom, acidic iodine atom, alkali metal atom and, optionally, tertiary amine (hereinafter "System B").

The addition of small amounts of ruthenium atom to System A to form System B resulted in an increase in the rate of formation of ethanol. However, the amount of ruthenium added must be controlled to preclude metal precipitation. Results appeared to indicate the molar ratio of I:Ru in the system exerted an effected on metal precipitation. Systems in which the Co:Ru molar ratio were the same but in which the I:Ru molar ratio was changed showed metal precipitation as the I:Ru molar ratio was decreased below certain values. It is theorized, though without being intended to be bound by theory, metal precipitation may be related to the iodine scavenging effect of ruthenium and the I:Ru molar ratio must be maintained at an adequate value so as to minimize metal precipitation.

The alkali metal atom source can be the same as that used in System A.

The temperature at which System B can be used varies from about 160° C. to about 230° C., preferably from about 170° C. to about 220° C., and most preferably from about 180° C. to about 210° C.

Solutions of System B were also stable and maintained their stability, homogeneity and catalytic activity to the same extent as previously discussed for System A. The ability to produce stable solutions of the catalyst systems under the conditions described was completely unexpected and unpredictable.

The use of System B in homologation of methanol with syngas to produce organic compounds has many advantages in addition to that of stability. This system has a high activity for the formation of ethanol, high selectivity to ethanol and high conversion rate as compared to known systems.

These beneficial results are achieved in batch operations and in continuous unit operations. Previous attempts to employ known systems in continuous units have often been precluded because of metal atom, or catalyst, precipitation problems. The presence of the alkali metal atom in Systems A and B as promoter inhibits precipitation and permits continuous operation at high conversion and selectivity.

The cobalt component can come from a number of sources such as any of the known cobalt carboxylates, e.g., cobalt formate, cobalt acetate, cobalt propionate, cobalt butyrate, cobalt valerate, cobalt hexonate, and the like; the known cobalt carbonyl compounds such as dicobalt octacarbonyl methyl cobalt tetracarbonyl, acetyl cobalt tetracarbonyl, methyl cobalt tetracarbonyl, acetyl cobalt tetracarbonyl, and the like, or their phosphine substituted analogs many of which are known to those skilled in the art; cobalt oxide and cobalt hydroxide; cobalt carbonate and cobalt bicarbonate; and the soluble cobalt halides such as cobalt iodide, cobalt bromide and cobalt chloride. In addition to those enumerated above, those skilled in this art are fully familiar with and aware of many other cobalt compounds which can be used.

The concentration of cobalt atom in the reactor when using either catalyst System A or catalyst System B is from about 0.00013 to about 0.4 mole per liter; preferably from about 0.013 to about 0.15 mole per liter.

The ruthenium which is used in the catalyst system can come from any source which is capable of providing soluble ruthenium atoms in the reaction. Illustrative of such ruthenium compounds one can name ruthenium trichloride, ruthenium tribromide, ruthenium triiodide, ruthenium acetate, ruthenium acetylacetonate, ruthenium propionate, ruthenium octanoate, ruthenium dioxide, ruthenium tetraoxide, ruthenium pentacarbonyl, triruthenium dodecacarbonyl and the like. These, as well as many others known to those skilled in this art can be used.

The concentration of ruthenium atom in the reactor when using catalyst System B is from about 0.008 to about 0.05 mole per liter; preferably from about 0.01 to about 0.045 mole per liter. The most preferred ruthenium atom concentration is about 0.025 to about 0.035 mole per liter.

Although many soluble halides may be used as a promoter in the catalyst system it is preferred that iodine or its derivatives be so employed. Illustrative as sources of the iodide atom are elemental iodine; cobalt iodide; hydrogen iodide; the alkyl iodides having from 1 to 10 carbon atoms such as methyl iodide, ethyl iodide, propyl iodide, 2-ethyhexyl iodide, n-decyl iodide, and the like. Any other source of iodide which will ionize to form free iodide ions in the reaction medium can be used as promoter. One can also employ any of the organic iodine compounds that will furnish iodide to the reaction medium. Further, one can use mixtures of iodine and/or iodide compounds, if so desired. The preferred source of the iodide is elemental iodine.

The concentration of acidic iodine atom in the reactor when using either catalyst System A or catalyst System B is from about 0.000013 to about 1.6 moles per liter; preferably from about 0.026 to about 0.6 mole per liter.

The alkali metal atom component of the catalyst system can come from any of the known ionic compounds of the alkali metals sodium, potassium, lithium, rubidium and cesium. The preferred are the sodium and potassium salts. Illustrative thereof one can mention sodium iodide, sodium bicarbonate, sodium carbonate, sodium nitrate, sodium nitrite, sodium sulfate, sodium bisulfate, sodium chromate, sodium permanganate, sodium chlorate, sodium persulfate, sodium tetraborate, sodium bromide, sodium chloride, sodium fluoride, sodium sulfite, sodium hypochlorite, as well as any other ionic salt of sodium. Rather than repeat the individual compound names, the corresponding potassium, lithium, rubidium and cesium salts are illustrative of useful ionic compounds.

The concentration of alkali metal atom in the reactor when using either catalyst System A or catalyst System B is from about 0.00013 to about 1 mole per liter; preferably from about 0.07 to about 0.6 mole per liter.

As indicated, an organic tertiary amino compound of the general formula $R_3N$ can optionally be present as co-promoter in the system. The use of such additives is known, as are their identities, to those skilled in this art. In this formula R represents an organic moiety. The additive can serve as a catalyst stabilizer and/or to further enhance efficiency, conversion rate and selectivity, especially when the reaction is carried out at higher temperature. The additive also serves to inhibit equipment corrosion in some instances. However, the use of the additive is not mandatory and the reaction can be carried out without it.

A large number of organic amines is known to those skilled in the art as useful and any of these can be used provided they do not have an adverse effect on the reaction. Among those of particular utility are the tertiary amines such as trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chlorophenyl)- amine, dibutyl phenylamine, dipentyl cyclopentylamine, ethyl diphenylamine, trinaphthylamine tri-p-tolylamine, tri-benzylamine, tri(3-methylcyclohexyl)amine, as well as other tertiary amines. These and many others are known in the art. They can be used singly or, if one desires, mixtures containing two or more ligands can be used.

As is known in this art, one can additionally have an inert solvent present in the reaction mixture Any of these inert solvents can be used and they are well known to those of ordinary skill in this art.

The concentration of the $R_3N$ ligand in the reactor, for either System A or System B, can vary from about 0.000013 to about 0.08 mole per liter; preferably from about 0.02 to about 0.04 mole per liter.

The mole atom ratio of Co:Ru can vary from about 0.5:1 to about 10:1, preferably from about 3:1 to about 7:1; of I:Ru from about 1:1 to about 30:1, preferably from about 3:1 to about 27:1; and of alkali metal atom M:Ru of from about 1:1 to about 30:1, preferably from about 2:1 to about 20:1 in System B.

In System A, the mole atom ratio of I:Co can vary from about 1:1 to about 6:1, preferably from about 2:1 to about 4:1; and of M:Co from about 1:4 to about 4:1, preferably from abut 1:2 to about 2:1.

Use of System A at temperatures up to about 180° C., preferably 165° C. to 180° C., favored the hydroformylation reaction; while at temperatures of from about 185° C. to about 225° C. or higher, preferably 190° C. to 220° C., the homologation reaction was favored.

System B can be carried out at temperatures of from about 150° C. to about 240° C. or higher, preferably from about 175° C. to about 215° C., with the homologation reaction occurring at these temperatures.

The pressure of the reaction can be from about 2,000 psig to 10,000 psig, preferably from 2,500 psig to 7,500 psig, most preferably from 4,000 psig to 6,000 psig.

The mole ratio of $H_2$:CO in the synthesis gas can vary from about 10:1 to 1:10, preferably from about 3:1 to 1:3.

The reaction time varies depending upon the reaction parameters, reactor size and charge, and the individual components employed at the specific process conditions. The reaction can be a batch or continuous reaction.

The batch experiments and examples detailed below were carried out in a Hastelloy ® steel stirred autoclave reactor having a volume of 300 ml, which was equipped with temperature and pressure sensing means, heating and cooling means, agitator and inlet and outlet means for introducing and removing components from the reactor. The autoclaves used in synthesis gas reactions are well known in the art and can be used in this process.

Prior to charging the reactants the autoclave was washed with methanol at 100° C. under a nitrogen gas pressure of 500 to 1,000 psig by agitating for 30 minutes. The autoclave was drained, rinsed with dry acetone, and dried with nitrogen. The liquid components were charged to the cleaned autoclave first and then the solid components were added and stirred. The autoclave was closed, purged with synthesis gas and then pressurized to the desired pressure with synthesis gas. The autoclave contents were heated to the selected temperature, with agitation (usually 750 rpm), in about 45 minutes. After the desired temperature was reached, the reaction was allowed to consume synthesis gas for the time period indicated. During this time the pressure was maintained by addition of synthesis gas as needed.

At the end of the reactor run, the contents were cooled, generally to about 10° C. A vapor phase sample was taken for gas chromatography analysis; the gas phase was vented through two dry-ice acetone traps and then through a 10 liter saturated solution of calcium hypochlorite to remove metal carbonyls, if formed. The reactor was pressurized three times with nitrogen, 90 psig, and vented through the same system.

The residual reactor contents were dumped into a chilled pressure bottle and sealed. Subsequent analysis was performed using a Hewlett-Packard Model 5880 gas chromatograph equipped with a one-eighth inch diameter by ten feet long column packed with Chromosorb 101.

In those examples in which the reaction was carried out in a single pass continuous reactor, a Hastelloy ® steel stirred autoclave was used having a volume of 300 ml. The equipment was supplied with reservoirs for the synthesis gas mixture and a methanol solution of the catalyst components, feed control and recovery means, temperature and pressure sensing means and heating and cooling means.

The premixed methanolic solution of the catalyst was continuously fed into the base of the autoclave and the syngas was sparged through a dip tube into the reactants solution. The mixture was continuously stirred and pressure and temperature were maintained. The two-phase mixture overflowed from the reactor through appropriate control valves into a high pressure separator and then to a low pressure separator for separation and recovery of products on a continuous basis.

The following examples serve to further illustrate this invention.

Example 1 (System A Catalyst)

A series of experiments was conducted at a pressure of 5,000 psig, a $H_2$:CO ratio of 1:1 and a temperature of 190° C. using the procedure and stirred autoclave described above. In each experiment the autoclave was charged with 75 ml of methanol, 8 mmoles of cobalt acetate and 16 mmoles of iodine plus the other components (in millimoles, mm) identified below. The reaction was continued for one hour with synthesis gas fed into the reactor to raise the pressure to the original 5,000 psig whenever the pressure dropped 200 psig. The major products are identified in Table I.

TABLE I

| Run | 1 | 2 | 3 | 4 |
|---|---|---|---|---|
| Sodium tetraborate | 0 | 1 | 4.2 | 10.5 |
| Tributylamine | 0 | 3 | 3 | 3 |
| Methanol Conversion, % | 76 | 88 | 85 | 95 |
| Products, Conversion Rate in M $hr^{-1}$ | | | | |
| Dimethyl ether (DME) | 2.1 | 0.08 | 0.75 | 0.03 |
| Acetaldehyde (AcH) | 2.0 | 1.1 | 3.2 | 2.1 |
| Ethanol (E) | 0.2 | 0.6 | 0.1 | 2.0 |
| Dimethylacetal (DMA) | 0.5 | 0.6 | 0.4 | 0.2 |
| Methyl acetate (MA) | 0.9 | 1.3 | 1.9 | 1.3 |
| Acetic acid (AA) | 0.4 | 0.4 | — | 1.5 |

In Table II are shown the results of a series of experiments in which the reaction time was twenty minutes. In this series the temperature, amount of cobalt acetate (CoAc) and the amount of iodine added were also modified.

TABLE II

| Run | 5 | 6 | 7 | 8 | 9 | 10 | 11 | 12 | 13 | 14 |
|---|---|---|---|---|---|---|---|---|---|---|
| Temp °C. | 165 | 165 | 165 | 165 | 165 | 165 | 170 | 180 | 190 | 155 |
| CoAc, mm | 8 | 8 | 8 | 4 | 4 | 8 | 8 | 8 | 8 | 8 |
| $I_2$, mm | 16 | 16 | 16 | 8 | 8 | 16 | 16 | 16 | 16 | 16 |
| $Na_2B_4O_7$, mm | 0 | 0 | 10.5 | 5.3 | 8 | 10.5 | 10.5 | 10.5 | 10.5 | 10.5 |
| $Bu_3N$, mm | 0 | 3 | 0 | 16 | 1.5 | 3 | 0 | 0 | 0 | 0 |
| Methanol Conv., % | 74 | 86 | 90 | 12 | 59 | 83 | 76 | 83 | 86 | 62 |
| Products, Conversion Rate in M $hr^{-1}$ | | | | | | | | | | |
| DME | 5.7 | 3.6 | 0.1 | — | 0.1 | 0.1 | 0.03 | 0.1 | 0.1 | 0.1 |

TABLE II-continued

| | | | | | | | | | |
|---|---|---|---|---|---|---|---|---|---|
| AcH | 9.9 | 12.3 | 10.6 | — | 3.2 | 12.8 | 9 | 5.2 | 1.22 | 3.8 |
| E | 0.1 | 0.2 | 0.5 | — | 0.4 | 1.4 | 1.3 | 5.6 | 10.3 | 0.1 |
| DMA | 10.7 | 6.4 | 5.9 | — | 11.6 | 4.4 | 1.0 | 4.1 | 0.8 | 9.4 |
| MA | 3.9 | 4.5 | 5.2 | 0.5 | 6.1 | 6.4 | 6.9 | 5.9 | 4.1 | 4.9 |
| AA | — | 0.2 | 0.5 | — | — | 3.6 | 1.7 | 0.9 | 0.8 | 0.4 |

The use of other sodium salts is shown in the series summarized in Table III. These runs were carried out in the manner described for Table II, at 165° C., using 8 mm of cobalt acetate, 16 mm of iodine and 21 mm of sodium; but without addition of tributylamine.

TABLE III

| Run | 15 | 16 |
|---|---|---|
| Sodium salt | NaI | NaHCO$_3$ |
| Methanol Conversion, % | 91 | 90 |
| Products, Conversion Rate in M hr$^{-1}$ | | |
| DME | 0.2 | 0.2 |
| AcH | 15.1 | 15.7 |
| E | 1.2 | 0.9 |
| DMA | 2.2 | 2.0 |
| MA | 4.8 | 5.1 |
| AA | 2.2 | 2.8 |

Table IV shows the effect of the presence of the alkali metal atom at higher reaction temperatures on the conversion rate to ethanol. In this series 4 mm of cobalt acetate and 8 mm of iodine were used in each experiment; reaction time was 20 minutes.

TABLE IV

| Run | 17 | 18 | 19 | 20 |
|---|---|---|---|---|
| Temp. °C. | 210 | 210 | 220 | 220 |
| Na$_2$B$_4$O$_7$, mm | 0 | 5.3 | 0 | 5.3 |
| Bu$_3$N | 0 | 1.5 | 0 | 1.5 |
| Methanol Conversion, % | 86 | 90 | 72 | 90 |
| Products, Conversion Rate in M hr$^{-1}$ | | | | |
| DME | 2.7 | 0.1 | 10.7 | 0.2 |
| AcH | 9.5 | 7.5 | 4.5 | 4.2 |
| E | 0.7 | 5.7 | 0.3 | 7 |
| DMA | 7.7 | 2 | 2.3 | 1.2 |
| MA | 1.8 | 3.4 | 2.4 | 3 |
| AA | — | 1.8 | — | 3.7 |

The comparison runs (those which did not contain added sodium atom) in Tables I to IV are Runs 1, 5, 6, 17 and 19.

Precipitation of cobalt metal was noted at 190° C. and 210° C. in Runs 1 and 17; this was not noted at these elevated temperatures when sodium was present in Runs 2 and 18. However, at 220° C. cobalt metal precipitation was noted even with the presence of the sodium metal in Run 20.

At 190° C. and 210° C. the conversion rate to ethanol was increased by the use of alkali metal atom and butyl amine ligand as shown by comparison of Run 1 with Runs 4 and 13 and Run 17 with Run 18.

At lower temperatures, 165° C. to 180° C., the hydroformylation reaction is favored as evidenced by the high conversion rates to acetaldehyde and dimethylacetal and a low conversion rate to ethanol, Runs 5 to 10 and 14, but their rates of formation were not enhanced by addition of the alkali metal atom in the form of sodium tetraborate. Similar enhanced results were obtained when the alkali metal atom source was sodium iodide or sodium bicarbonate; however, in these instances the hydroformylation reaction was enhanced, compare Runs 15 and 16 to Run 5.

Example 2 (System B Catalyst)

The effect of the addition of ruthenium atom to the reactor was quite noticeable, the conversion rate almost doubled. In these experiments the stirred autoclave was charged with 53 ml of methanol, 8 mm of cobalt acetate, 16 mm of iodine, 10 mm of sodium tetraborate and 3 mm of tributylamine; also present in Run 2 was 0.4 mm of triruthenium dodecacarbonyl. The reaction was carried out at 180° C. for 20 minutes at a pressure of 5,000 psig and using a H$_2$:CO mole ratio of 1:1 in a manner similar to that previously described in Example 1. The results are summarized in Table V.

TABLE V

| Run | 1 | 2 |
|---|---|---|
| Methanol Conversion, % | 83 | 92 |
| Products, Conversion Rate in M hr$^{-1}$ | | |
| DME | 0.1 | 0.08 |
| E | 5.6 | 11.3 |
| Ethylacetate | — | 3.5 |
| MA | 5.9 | 4.4 |
| AA | 0.9 | 2.5 |

A further series of reactions was carried out at 210° C. adding the amounts of reactants, in millimoles, shown below, to the methanol.

TABLE VI

| Run | 3 | 4 | 5 | 6 | 7 |
|---|---|---|---|---|---|
| Cobaltacetate, mm | 4 | 4 | 4 | 4 | 4 |
| Iodine, mm | 8 | 8 | 12 | 12 | 12 |
| Na$_2$B$_4$O$_7$, mm | 5.3 | 8 | 0 | 0 | 0 |
| NaHCO$_3$, mm | 0 | 0 | 8 | 16 | 24 |
| Tributylamine, mm | 1.5 | 1.5 | 0 | 0 | 0 |
| Ru$_3$(CO)$_{12}$, mm | 0.4 | 0.4 | 0.8 | 0.8 | 0.8 |
| Methanol Conversion, % | 79 | 59 | 90 | 76 | 31 |
| Products, Conversion Rate in M hr$^{-1}$ | | | | | |
| DME | 0.2 | 0.2 | 0.4 | 0.2 | 0.08 |
| E | 18.7 | 12.3 | 16 | 17.8 | 1.4 |
| DMA | 1.2 | 1 | 2.3 | 1.2 | 0.3 |
| MA | 2 | 3.1 | 1.9 | 2.3 | 0.7 |
| AA | 0.5 | — | 1 | — | — |

The low conversion to ethanol (E) in Run 7 is believed to be the result of the higher than desired Na:Ru mole ratio. This high mole ratio serves to inhibit the homologation reaction but not the hydroformylation reaction.

For comparative purposes a series was performed which was free of alkali metal atom and tributylamine; this is summarized in Table VII.

TABLE VII

| Run | 8 | 9 | 10 | 11 | 12 |
|---|---|---|---|---|---|
| Cobaltacetate, mm | 4 | 4 | 4 | 4 | 4 |
| Iodine, mm | 8 | 8 | 2 | 12 | 12 |
| Ru$_3$(CO)$_{12}$, mm | 0.4 | 0.8 | 0.4 | 0.4 | 0.8 |
| Methanol Conversion, % | 97 | 96 | 71 | 97 | 88 |
| Products, Conversion Rate in M hr$^{-1}$ | | | | | |
| DME | 1.5 | 2.8 | 0.7 | 3.1 | 3.8 |
| E | 14.4 | 13.4 | 13.1 | 12.9 | 1.46 |
| DMA | 3.2 | 1.5 | 0.7 | 3.3 | 2 |
| MA | 1.1 | 2.4 | 1.3 | 1.5 | 2.4 |

TABLE VII-continued

| AA | 1.5 | 0.7 | 0 | 2.3 | 0.7 |

As shown by the results, the addition of 0.4 mmole of ruthenium atom almost doubled the conversion rate (Runs 1 and 2).

The System B catalyst used in Runs 1 to 7 gave high conversion rate while simultaneously decreasing the amount of dimethyl ether (DME) produced.

Example 3

In this example, a series of reactions was carried out in which the catalyst solution was prepared beforehand and its stability was evaluated. It was observed the solutions kept their homogeneity for several days after a catalytic run and did not precipitate solids even after standing at ambient temperature for several days. Nor did the catalytic activity of the catalytic mixtures treated in this manner alter upon standing. This previously unknown treatment is capable of providing stable catalyst solutions that can be stored at ambient conditions for several days prior to use; a feature highly desirable in continuous processes.

The treatment of the components to produce the stable catalyst compositions was performed by preparing a solution of the system's components in methanol, precooking the solution at about 90° C. to 100° C. for 10 minutes at a $H_2$:CO (1:1 mole ratio) pressure of 5,000 psig and cooling to ambient temperature. The solution was checked for solids with no evidence thereof observed on storage. For each 53 ml. of methanol, the amounts of each compound present in the solution are shown in Table VI. It should the noted that the temperature can be varied to from about 75° C. to about 125° C. and the pressure from 2,000 psig to 10,000 psig. The stabilized catalyst solutions were used to homologate methanol under conditions similar to those described in Example 1 with 1.5 mmoles of tributylamine added to the reaction in each case.

TABLE VI

| Run | 1 | 2 | 3 | 4 | 5 | 6 |
|---|---|---|---|---|---|---|
| Cobaltacetate, mm | 8 | 4 | 4 | 4 | 4 | 4 |
| Iodine, mm | 16 | 16 | 16 | 16 | 8 | 8 |
| Na$_2$B$_4$O$_7$, mm | 10.5 | 5.3 | 5.3 | 5.3 | 5.3 | 5.3 |
| Ru$_3$(CO)$_{12}$, mm | 0 | 0 | 2 | 4 | 4 | 4 |
| Solids after precook storage | 0 | 0 | 0 | 0 | 0 | 0 |
| time, hrs. | 88 | 24 | 24 | 24 | 36 | 90 |
| Products, Conversion Rate in M hr$^{-1}$ | | | | | | |
| AcH | 12.6 | 10.8 | 3.3 | 3.7 | 2.2 | 0.3 |
| DMA | 4.8 | 5 | 4.3 | 5.8 | 3 | 0.1 |
| E | 0.84 | 0.69 | 4.7 | 6.3 | 11.7 | 20.2 |
| MA | 6.1 | 6.1 | 4.9 | 5.2 | 4.8 | 3.2 |

The homologation reactions were carried out at 165° C. for Runs 1 to 4, at 185° C. for Run 5 and 210° C. for Run 6. The stored, precooked catalyst solution used in Run 1 showed the presence of 0.6 g of solid material that was identified as undissolved sodium metaborate, probably due to the higher sodium metaborate concentration present in this run.

As previously indicated, the lower temperature of 165° C. with catalyst System A in Runs 1 and 2 favored the hydroformylation reaction with formation of acetaldehyde and dimethyl acetal dominating and the rate of formation of ethanol being much lower. As the temperature was increased and with the presence of ruthenium metal atom (Runs 3 to 6) the homologation reaction dominates and the conversion rate to formation of ethanol increases.

Runs 5 and 6 were carried out in a single pass continuous reactor, whereas Runs 1 to 4 were batch reactions.

What is claimed is:

1. An improved process for the production of ethanol by the reaction of methanol with synthesis gas in contact with a homogeneous catalyst system consisting of cobalt, ruthenium, iodine and an alkali metal at a pressure of from 2,000 psig to 10,000 psig and a temperature of from about 180° to about 210° C., wherein the mole atom ratio of Co:Ru is from 3:1 to 7:1, the mole ratio of alkali metal atom M:Ru is from 2:1 to 20:1 and the mole atom ratio of I:Ru is from 3:1 to 27:1, the concentration of cobalt in the reactor 0.013 is from to 0.15 mole per liter, the concentration of ruthenium in the reactor is from 0.025 to 0.035 mole per liter, the concentration of iodine in the reactor is from 0.026 to 0.6 mole per liter, the concentration of alkali metal in the reactor is from 0.7 to 0.6 mole per liter, and the source of the alkali atom being sodium iodide, sodium bicarbonate or sodium tetraborate.

2. An improved process for the production of ethanol by the reaction of methanol with synthesis gas in contact with a homogeneous catalyst system consisting of cobalt, ruthenium, iodine, at least one organic amine and at least one alkali metal at a pressure of from 2,000 psig to 10,000 psig and a temperature of from about 180° to about 210° C., wherein the mole atom ratio of Co:Ru is from 3:1 to 7:1, the mole ratio of alkali metal atom M:Ru is from 2:1 to 20:1 and the mole atom ratio of I:Ru is from 3:1 to 27:1, the concentration of cobalt in the reactor is from 0.013 to 0.15 mole per liter, the concentration of ruthenium in the reactor is from 0.025 to 0.035 mole per liter, the concentration of iodine in the reactor is from 0.026 to 0.6 mole per liter, the concentration of alkali metal in the reactor is from 0.7 to 0.6 per liter, the source of the alkali atoms being sodium iodide, sodium bicarbonate or sodium tetraborate, the catalyst system containing from 0.02 to 0.04 mole per liter of an organic amine, and the organic amine being selected from the group consisting of trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)-amine, tri(p-chlorophenyl)-amine, dibutyl phenylamine, diphentyl cyclopentylamine, ethyl diphenylamine, trinaphthylamine, tri-p-tolylamine, tri-benzylamine, tri(3-methylcyclohexyl)amine, and a mixture of two or more of said organic amines.

* * * * *

UNITED STATES PATENT AND TRADEMARK OFFICE
CERTIFICATE OF CORRECTION

PATENT NO. : 4,954,665

DATED : September 4, 1990

INVENTOR(S) : Jose L. Vidal

It is certified that error appears in the above-identified patent and that said Letters Patent is hereby corrected as shown below:

Column 2, line 25, "No. 306,091" should read -- 4,306,091--.

Column 12, line 24, "0.013 is from" should read -- is from 0.013--.

Column 12, line 56, "diphenytl" should read -- dipentyl --.

Signed and Sealed this

Seventh Day of April, 1992

Attest:

HARRY F. MANBECK, JR.

*Attesting Officer*     *Commissioner of Patents and Trademarks*